United States Patent [19]

Kropp

[11] 4,007,040
[45] Feb. 8, 1977

[54] HARD COPPER FREE DENTAL GOLD ALLOYS

[75] Inventor: Rudolf Kropp, Pforzheim-Wurm, Germany

[73] Assignee: Deutsche Gold- und Silber-Scheideanstalt vormals Roessler, Frankfurt, Germany

[22] Filed: Jan. 27, 1976

[21] Appl. No.: 652,858

[30] Foreign Application Priority Data

Mar. 5, 1975 Germany .......................... 2509476

[52] U.S. Cl. ................................................. 75/165
[51] Int. Cl.² .......................................... C22C 5/02
[58] Field of Search ...................................... 75/165

[56] References Cited

UNITED STATES PATENTS

| | | | |
|---|---|---|---|
| 2,304,416 | 12/1942 | Leuser | 75/165 |
| 3,340,050 | 9/1967 | Nielsen et al. | 75/165 |
| 3,679,402 | 7/1972 | Hirschhorn | 75/165 |
| 3,819,366 | 6/1974 | Katz | 75/165 X |

*Primary Examiner*—C. Lovell
*Assistant Examiner*—E. L. Weise
*Attorney, Agent, or Firm*—Cushman, Darby & Cushman

[57] ABSTRACT

A hard, copper free gold alloy for dental purposes is prepared containing 61 to 85 weight % gold, 8 to 15 weight % platinum, 0 to 4 weight % palladium, 5 to 15 weight % silver and 2 to 5 weight % zinc. 0.05 to 0.1 weight % of the platinum can be replaced by iridium.

9 Claims, No Drawings

HARD COPPER FREE DENTAL GOLD ALLOYS

The invention is directed to copper free gold alloys suitable for dental purposes and based on gold, platinum and silver which contain zinc as the sole non-noble metal.

Alloys containing gold as the main constituent are needed in the dental industry for the production of bridges and cast protheses which are absolutely corrosion and tarnish resistant in the milieu of the mouth, but which at the same time must have a high degree of hardness in order to be equal to the chewing forces in the mouth in order to avoid deformation, fractures and too strong wear and tear.

It has been known for a long time that the necessary hardness of these gold alloys can be attained by addition of copper and silver and additionally metals of the platinum group, preferably platinum and/or palladium. Furthermore, it is known to also add nickel as an additional metal. A small addition of iridium in the known alloys serves to produce a fine grained structure.

However, on account of their copper content the known alloys have the disadvantage that they frequently have brown, black or blue tarnished coatings which chiefly consist of copper sulfide and strongly detract from the appearance of a prosthetic work. This appearance occurs after a short time of use in the mouth if there arises a thin copper precipitate on the alloy surface because of local element formation which is colored under the influence of sulfur containing foods with formation of sulfide. The copper originates from the copper containing solid solution crystals of the alloy which are stable in themselves, out of which it is diffused, for example, with oxide formation upon heating in air and has collected on the surface or in hardened cavities. This copper oxide goes into solution in the acidification but can be again separated on the alloy surface as metallic copper in the exchange of the alloy portion with a non-noble metal forceps if nitric acid is not used in the mouth there are gaps, for example, between alloy and synthetic resin or between two telescopic crowns, or especially with not entirely unobjectionable castings, surface cavities and porosities, which lead to the formation of oxygen cells on account of concentration differences of oxygen in the saliva inside and outside the cavities. These oxygen cells precipitate metallic copper in thin layers on the alloy surface after the copper is previously dissolved out from copper oxide occlusions or directly from the outermost layers of the alloy, and are starting points for a subsequent coloration.

There have already been described hard, copper-free dental gold alloys in which in place of copper for the production of the desired hardness there are used either cobalt, iron and/or nickel as alloying additives (German Offenlegungsschrift 2,136,232) or indium, tin and zinc (Wagner, German Offenlegungsschrift 2,139,331). Alloys of the named type have proven mouth and tarnish resistant, but additives of cobalt, iron, nickel, indium or tin have the disadvantage that the alloys become coated with oxide layers in the casting or annealing, which coatings are only dissolved with difficulty with the dilute acids useable in the dental art (hydrochloric acid, sulfuric acid or sulfamic acid). This especially causes noticeable disturbances in the frequently necessary soldering since the flux used hereby likewise only dissolves out the oxides of the named additive metals slowly and to a limited extent.

Therefore, it was the problem of the present invention to develop a copper free gold alloy suitable for dental purposes which must be mouth and tarnish stable, but which does not permit the coating with disturbing oxide layers in the casting and annealing. Besides these alloys must be sufficiently hard.

This problem was solved, according to the invention, by using gold alloys which contain 61 to 85 weight % gold, 8 to 15 weight % platinum, 0 to 4 weight % palladium, 5 to 15 weight % silver and 2 to 5 weight % zinc.

These alloys of the invention are absolutely mouth and tarnish stable and after a heat treatment attain high heat values. In the range of 8 to 11 weight % platinum, 0 to 1 weight % palladium and 2 weight % zinc they are particularly useful for crown rings, crown caps and cast fillings, since in this alloy range they do not show extreme hardness values.

Particularly high hardness values are reached with alloys that contain 69 to 72 weight % gold, 11 to 14 weight % platinum, 2 to 4 weight % palladium, 9 to 12 weight % silver and 2.5 to 4 weight % zinc. Such alloys exhibit in the soft annealed and cooled condition hardnesses of at least 140 Vickers units and in the hardened condition at least 200 Vickers units. With these copper free alloys of the invention there are obtained hardness values of copper containing dental gold alloys, without having to take into consideration the disadvantages of the copper containing alloys in regard to corrosion susceptibility.

In the following table there are set forth the compositions and hardness values of several particularly advantageous alloys.

| Content in Weight % | | | | | | Melting Interval in ° C. | VICKERS HARDNESS HV | |
|---|---|---|---|---|---|---|---|---|
| Au | Pt | Pd | Ag | Zn | Ir | | Annealing 15 minutes at 800 ° C. Quenching in Water | Annealing 15 minutes at 800° C. Quenching in Water and hardening 15 minutes at 500° C. |
| 72 | 12. | 3.0 | 10 | 3.0 |  | 1140 – 1020 | 143 | 220 |
| 72 | 11.9 | 3.0 | 10 | 3.0 | 0.1 | 1140 – 1020 | 143 | 220 |
| 71 | 13 | 2.5 | 10 | 3.5 |  | 1130 – 1010 | 183 | 243 |
| 71 | 13.9 |  | 10 | 5.0 | 0.1 | 1030 – 930 | 127 | 210 |
| 70 | 13 | 1.0 | 10 | 5.0 |  | 1080 – 970 | 148 | 210 |
| 70 | 13 | 3.0 | 10 | 4.0 |  | 1110 – 970 | 161 | 243 |
| 70 | 12.9 | 3.0 | 10 | 4.0 | 0.1 | 1110 – 970 | 161 | 243 |
| 70 | 13 | 3.5 | 10 | 3.5 |  | 1140 – 1020 | 161 | 243 |
| 72 | 9.9 | 1.0 | 15 | 2.0 | 0.1 | 1140 – 1010 | 103 | 161 |
| 70 | 14 | 3.0 | 10 | 3.0 |  | 1150 – 1030 | 143 | 220 |
| 70 | 13.9 | 3.0 | 10 | 3.0 | 0.1 | 1150 – 1030 | 143 | 220 |

By the addition of 0.05 to 0.1 weight % of iridium in the form of a Pt-Ir prealloy the structure of the alloys of the invention can be made substantially fine grained without disadvantageously affecting the other properties. The number of grains can be increased therethrough from about 100 grains/mm$^2$ up to 1500 grains/mm$^2$.

The alloys of the invention contain as the sole non-noble metal 2 to 5 weight % zinc whose oxide is very easily dissolved in dilute acids and in solder fluxes and, therefore, cause no difficulties in manufacturing. In contrast to copper, zinc as the alloying additive gives little cause for coloration while the alloy is worn in the mouth. Through the high Pt portion the alloy of the invention has a light yellow color, in contrast to the frequently reddish tone of copper containing gold alloys, and therefore approaches the desire of many dentists and patients for a more toothlike color.

By the addition of only 2 to 5 weight % of zinc, it has been unexpectedly found possible to produce the high hardness value of the copper containing dental gold alloys without having the negative properties of the copper alloys.

Unless otherwise indicated all parts and percentages are by weight.

The alloy can consist essentially of or consist of the stated materials.

What is claimed is:

1. A hard copper free gold alloy suitable for dental purposes consisting essentially of (a) 61 to 85 weight of gold, 8 to 15 weight % platinum, 0 to 4 weight % palladium, 5 to 15 weight % silver and 2 to 5 weight % zinc or (b) an alloy as defined in (a) with 0.05 to 0.1 weight % of the platinum replaced by iridium.

2. The composition of claim 1 containing (a) 69 to 72 weight % gold, 11 to 14 weight % platinum, 2 to 4 weight % palladium, 9 to 12 weight % silver and 2.5 to 4 weight % zinc or (b) the alloy as defined in (a) with 0.05 to 0.1 weight % of the platinum replaced by iridium.

3. The composition of claim 2 which is (a).

4. The composition of claim 2 which is (b).

5. The composition of claim 1 which is (a).

6. The composition of claim 1 which is (b).

7. The composition of claim 1 which consists essentially of (a) 61 to 85 weight % gold, 8 to 11 weight % platinum, 0 to 1 weight % palladium, 5 to 15 weight % silver and 2 weight % zinc or (b) the alloy as defined in (a) with 0.05 to 0.1 weight % of the platinum replaced by iridium.

8. The composition of claim 7 which is (a).

9. The composition of claim 8 which is (b).

* * * * *